United States Patent [19]

Pyles

[11] Patent Number: 5,133,097
[45] Date of Patent: Jul. 28, 1992

[54] SHEETS FOR OPERATING TABLE WITH ARM RESTS

[76] Inventor: Stephen Pyles, 1303 S.E. 59th St., Ocala, Fla. 32671

[21] Appl. No.: 628,096

[22] Filed: Dec. 17, 1990

[51] Int. Cl.$^5$ .................. A47G 9/02; A61G 13/12; A61G 13/10; A61G 13/00
[52] U.S. Cl. .................................. 5/623; 5/618; 5/600; 5/482; 5/487; 5/497; 297/227
[58] Field of Search ............ 5/487, 497, 482, 490, 5/623, 600, 618; 269/328, 322; 297/227, 229; 378/208, 209; 150/158

[56] References Cited

U.S. PATENT DOCUMENTS

| | | | |
|---|---|---|---|
| 2,258,782 | 10/1941 | McKean | 269/328 |
| 2,942,280 | 6/1960 | May, Jr. | 5/497 |
| 3,452,978 | 7/1969 | Creelman | 269/328 |
| 4,536,028 | 8/1985 | Jones et al. | 5/497 |
| 4,704,753 | 4/1987 | Lunt | 5/487 |

FOREIGN PATENT DOCUMENTS

| | | | |
|---|---|---|---|
| 70118 | 2/1915 | Switzerland | 5/502 |
| 744618 | 2/1956 | United Kingdom | 297/227 |
| 823414 | 11/1959 | United Kingdom | 297/227 |

*Primary Examiner*—Alexander Grosz
*Attorney, Agent, or Firm*—Dominik, Stein, Saccocio, Reese, Colitz and Van Der Wall

[57] ABSTRACT

The present invention is directed to an improved sheeting system for covering an operating table which includes a main body section with a head section and a foot section pivotally coupled about horizontal axes to the main body section, and with sidearms pivotally coupled about vertical axes to the main body section, the sheeting system including a single large sheet positionable over the main body section, head section and foot section formed of a non-woven fabric having an enlarged planar portion, downwardly turned edges and an inwardly turned periphery with elastomeric material coupled to at least portions of the periphery whereby the edges and periphery accommodate the bending of the sheet along its side edges with the bending of the operating table; and a pair of small sheets positionable over the side arms.

16 Claims, 3 Drawing Sheets

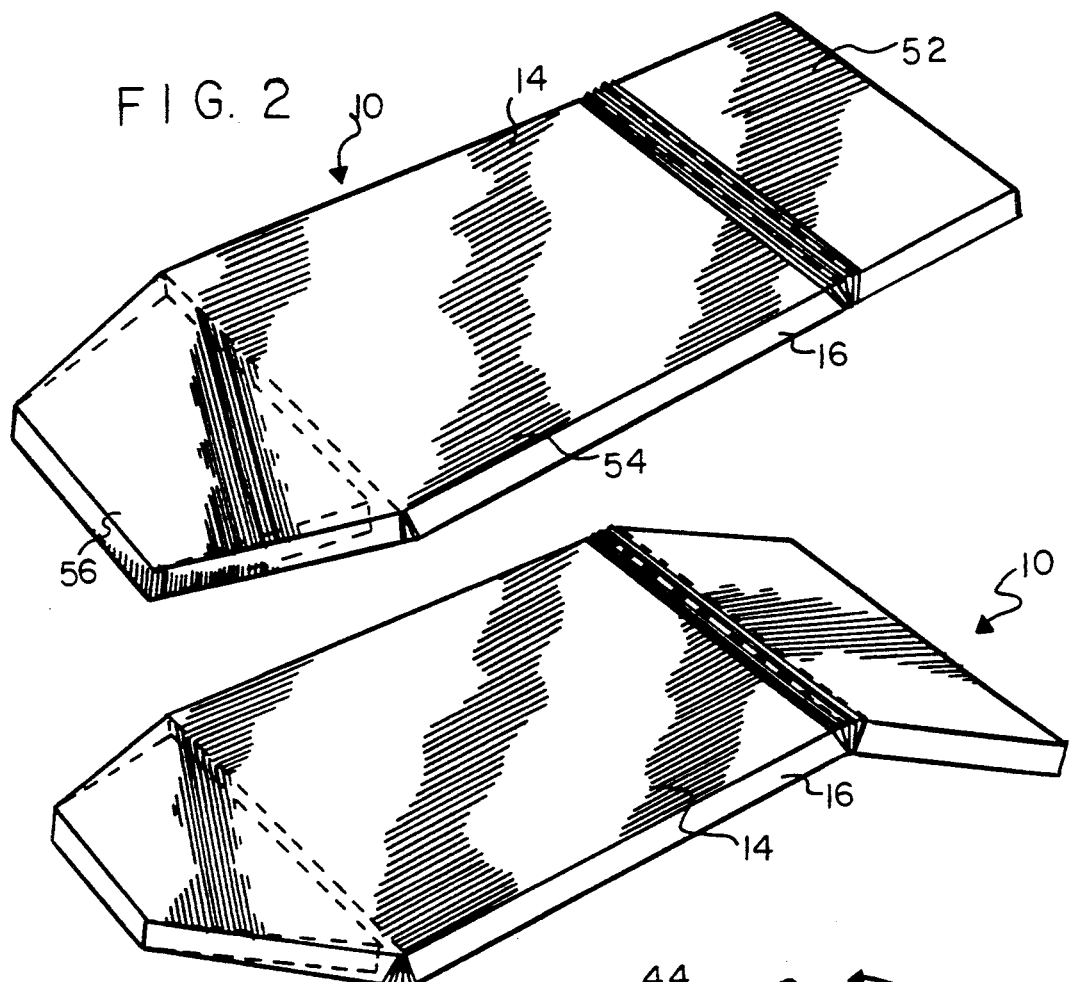

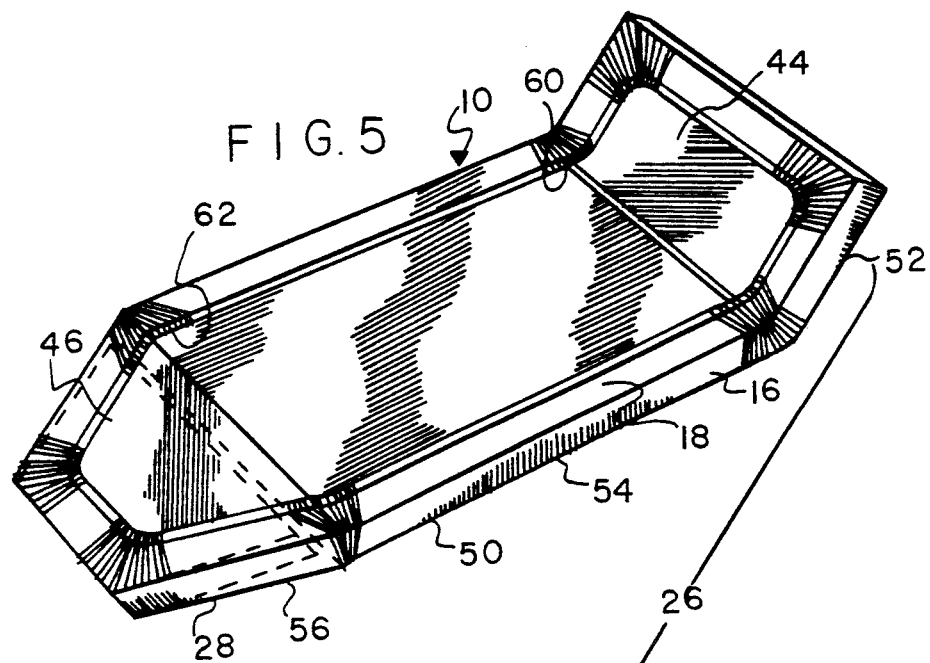
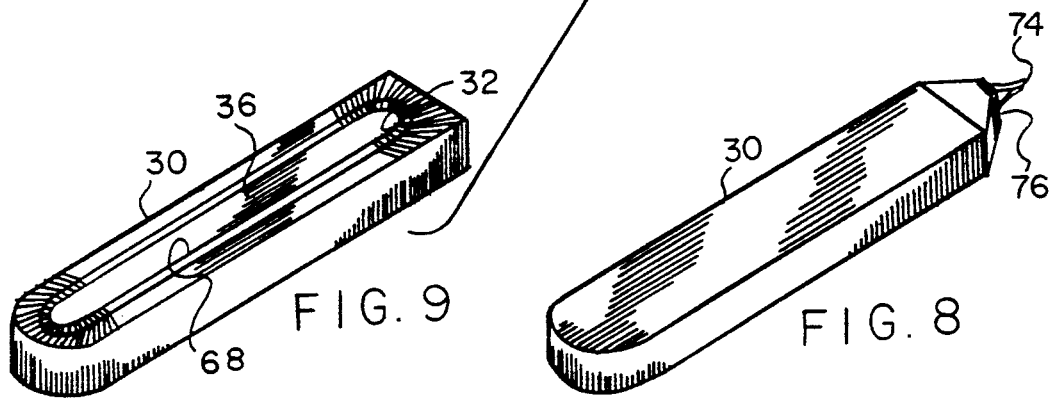
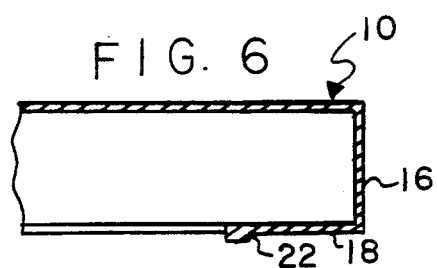
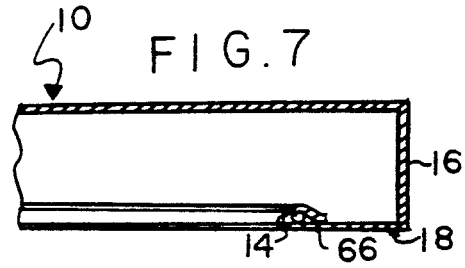

SHEETS FOR OPERATING TABLE WITH ARM RESTS

BACKGROUND OF THE INVENTION

This invention relates to sheets for operating tables and, more particularly, to sheets constructed of non-woven fibers and with peripheral portions provided with elastic to thereby constitute filled sheets and with central regions adapted to accommodate the bending of the operating table to which they are fitted.

DESCRIPTION OF THE PRIOR ART

There is an ever increasing trend in hospitals to eliminate woven cloth for a wide variety of functions and to use paper or other non-woven fabric as a substitute. Such functions include clean up cloths, dressing gowns, etc. One function where woven cloth is still utilized is as a cover or sheet for operating tables. When woven cloth is used as a cover for operating tables, it has the benefits of efficiently absorbing associated fluids such as blood, of keeping the operating table clean, of promoting sanitation, etc. Unfortunately, the use of woven cloth has the detriments of high costs in terms of time and money associated with laundering, storage space, large inventories, etc.

Various devices are commercially used and are disclosed in the patent literature for accommodating patients in and around a hospital, including in and around an operating room. By way of example, multilayer covers for various support structures are disclosed in U.S. Pat. No. 4,923,453 to Bullard which discloses a multilayer absorbant disposable cover for X-ray tables; U.S. Pat. No. 4,358,865 to Pagel which discloses a multilayer sheet for use on stretchers; U.S. Pat. No. 4,744,118 to Lunt which discloses a multilayer sheet for use on crib mattresses as well as U.S. Pat. No. 4,627,426 to Wegener which discloses a multilayer sheet for use on operating tables. In all of these patents, the sheet material is a complex, multipart laminate adapted to be supported on a flat planar surface.

In addition to the foregoing, a use of a single layer sheet is disclosed in U.S. Pat. No. 3,765,040 to Holstein. The layer, however, is for use on a flat planar cot and is of a spunbonded olefin. Further, this patent discusses the unacceptability of paper for such sheeting functions.

Further, U.S. Pat. No. 3,503,391 to Melges discloses a non-woven surgical shield or cover member adapted to be draped over a patient. The cover has a plurality of pockets, slits, etc., to facilitate the operating on the patient over which the member is draped.

In addition, U.S. Pat. No. 4,041,203 to Brock discloses a fabric, per se, the fabric being of the type suitable or use as the material in the sheets of the present invention. Its use in fitted sheets in, however not disclosed, suggested or implied.

Lastly, conventional fitted sheets for home use are fabricated of woven cloth with their corners contoured so as to conform to the shape of the matress or box spring over which they are positioned. The corners are gathered and provided with an elastic member stitched thereto for accommodating their putting on and taking off. Nothing allows for the stretching of the fabric on the sides as would be required by the bending of a matress or an operating table.

As evidenced by the above referred to patents as well as other commercial devices, a wide variety of devices have been designed for use in the covering of surfaces in hospitals and operating rooms. No prior patent or commercial device, however, is directed to the use of non-woven fitted sheets on operating tables as disclosed and claimed herein.

Accordingly, it is an object of the present invention to provide an improved sheeting system for covering an operating table which includes a main body section with a head section and a foot section pivotally coupled about horizontal axes to the main body section, and with sidearms pivotally coupled about vertical axes to the main body section, the sheeting system including a single large sheet positionable over the main body section, head section and foot section formed of a non-woven fabric having an enlarged planar portion, downwardly turned edges and an inwardly turned periphery with elastomeric material coupled to at least portions of the periphery whereby the edges and periphery accommodate the bending of the sheet along its side edges with the bending of the operating table; and a pair of small sheets positionable over the side arms.

It is a further object of the present invention to ease the burden of hospital and operating room personnel before, during and after the treatment of a patient on the operating table.

It is a further object of the present invention to improve the sanitation of operating rooms.

It is a further object of the invention to provide gathered material and elastic on the sides of fitted sheets to allow for their bending with the bending of the operating table.

It is a further object of the invention to cover an operating table with a sheeting system which includes both a main sheet as well as auxiliary sheets for the arm boards.

Lastly, it is an object of the present invention to reduce time and cost associated with the storing and laundering of operating table sheets.

These objects and advantages should be construed as merely illustrative of some of the more prominent features and applications of the present invention. Many other beneficial results can be attained by applying the disclosed invention in a different manner or by modifying the invention within the scope of the disclosure. Accordingly, other objects and advantages as well as a fuller understanding of the invention may be had by referring to the summary and detailed description of the preferred embodiment of the invention in addition to the scope of the invention as defined by the claims taken in conjunction with the accompanying drawings.

SUMMARY OF THE INVENTION

The invention is defined by the appended claims with the specific embodiment shown in the attached drawings. For the purpose of summarizing an invention, the invention may be incorporated into an improved sheeting system for covering an operating table which includes a main body section with a head section and a foot section pivotally coupled about horizontal axes to the main body section, and with sidearms pivotally coupled about vertical axes to the main body section, the sheeting system including a single large sheet positionable over the main body section, head section and foot section formed of a non-woven fabric having an enlarged planar portion, downwardly turned edges and an inwardly turned periphery with elastomeric material coupled to at least portions of the periphery whereby the edges and periphery accommodate the bending of the sheet along its side edges with the bending of the operating table; and a pair of small sheets positionable over the side arms.

The small sheets are formed of a non-woven material with an enlarged planar portion, downwardly turned edges and inwardly turned portions. The inwardly turned portion may terminate in a periphery with a piece of elastomeric material attached to the periphery or in a periphery with a hem and a piece of elastomeric material within the hem or the small sheets may be formed in a tubular configuration. The elastomeric material may be attached to spaced portions of the periphery of the large sheet or the elastomeric material may be a single member located in a hem around the entire periphery of the large sheet.

The invention may be incorporated into a sheet for an operating table formed of a non-woven material having an enlarged planar portion, downwardly turned sides and an inwardly turned periphery with a piece of elastomeric material coupled to the periphery at the corners and at least partially down the sides to accommodate bending.

The sheet is of a non-extensible material. The sheet may be a single layer of paper or include a synthetic material. The inwardly turned portion may terminate in a periphery with pieces of elastomeric material attached to the periphery at spaced apart regions. The pieces of elastomeric material include a large piece extending from one side, around the head end and down the other side and a pair of small pieces on opposite sides. The inwardly turned portion may terminate in a periphery with a hem and a single piece of elastomeric material within the hem.

The foregoing has outlined rather broadly the more pertinent and important features of the present invention in order that the detailed description of the invention that follows may be better understood whereby the present contribution to the art may be more fully appreciated. Additional features of the invention will be described hereinafter which form the subject of the claims of the present invention. It should be appreciated by those skilled in the art that the conception and the specific embodiments disclosed herein may be readily utilized as a basis for modifying or designing other methods and apparatus for carrying out the same purposes of the present invention. It should also be realized by those skilled in the art that such equivalent methods and apparatus do not depart from the spirit and scope of the present invention as set forth in the appended claims.

DETAILED DESCRIPTION OF THE DRAWINGS

Shown in the various drawings are non-woven sheets for operating tables embodying the principals of the present invention.

FIG. 2 is a top perspective view of a non-woven fitted sheet positioned upon an operating table of FIG. 1.

FIG. 3 is a top perspective view of a non-woven fitted sheet, similar to FIG. 2, but with the sheet and operating table in a bent configuration.

FIG. 4 is a bottom perspective view of a non-woven fitted sheet positioned upon an operating table of FIG. 1.

FIG. 5 is a bottom perspective view of a non-woven fitted sheet, similar to FIG. 4, but with the sheet and operating table in a bent configuration.

FIG. 6 is a sectional view of through a portion of the sheet and periphery of the embodiment of the prior Figures.

FIG. 7 is a sectional view of through a portion of the sheet and periphery of the alternate embodiment of the invention.

FIG. 8 is a top perspective view of a non-woven fitted sheet, similar to FIG. 2, but fitted onto an armboard.

FIG. 9 is a bottom perspective view of a non-woven fitted sheet positioned upon an armboard.

Similar reference numerals refer to similar parts throughout the various Figures.

DETAILED DESCRIPTION OF THE INVENTION

Figure 1:
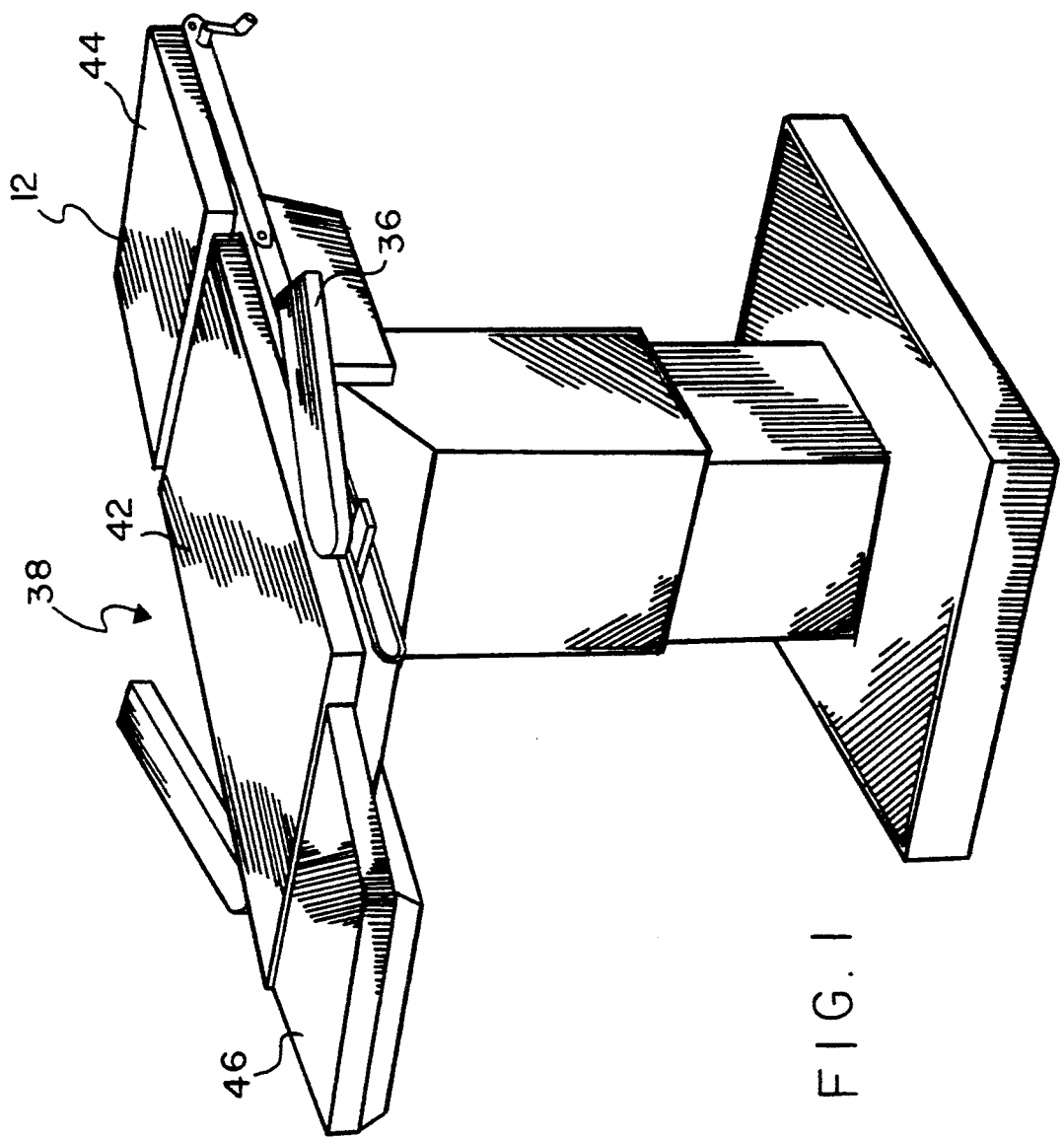
FIG. 1 is a perspective illustration of an operating table fitted with a fitted non-woven sheet constructed in accordance with the principles of the present invention.

Shown in the Figures, with particular reference to FIG. 1, the present invention is illustrated as a fitted sheet 10, or more specifically, fitted sheets, positionable on an operating table 12 and releasably secured thereto. Each fitted sheet is fabricated throughout the major extent 14 solely from a paper or other non-woven, inextensible material and is formed with down turned sides or edges 16 and inturned sides or edges 18. An elastic string or member 22 is located at the periphery, around the inturned edges of the material for securing the sheet in position over the entire upper surface and sides of the operating table during operation and use. The plurality of sheets together constitute a system 26 of one large main sheet 28, and two smaller or auxiliary sheets 30. Like the main sheet, the auxiliary sheets are formed of non-woven material with a peripheral elastic string 32, for being simultaneously positioned over the entire upper surfaces of operating table sideboards 36 while the main sheet is positioned over the operating table 12. The operating table and the sideboards together form a operating table system 38.

The operating table system is of the type commonly used in operating rooms today. The operating table itself includes a central rectangular main body section 42 for the torso of the patient to be operated upon. Two additional sections are pivotally secured to the upper and lower ends of the main body section. These two additional sections are the foot section 44 and the head section 46. The foot section has an upper or interior edge having a width substantially equal to the width of the main body section of the operating table. Like the main body section, the foot section is also rectangular but is of a length substantially less than the length of the main body section. The other section of the operation table is the head section which is shaped in the form of a trapezoid. The large parallel edge is pivotally attached to the upper or head end of the main body section and is of a width substantially equal top the width of the main body section. Its small parallel edge is of a reduced width. The non parallel sides are symetric and couple the upper and lower edges of the trapezoidal head section.

As used herein, the term lower refers the direction toward, or portion most closely adjacent to, the end of the foot section remote from the main body section. Similarly, the term upper refers to the direction toward, or portion most closely adjacent to, the end of the head section remote from the main body section.

In association with the main body section of the operating table, armboards 36 are provided. Each armboard is a rectangular member, one armboard being located on each side of the main body section. The upper surface of the armboards are essentially co-planar with the upper surface of the main body section. The foot section and head section may be pivoted from the plane of the main body portion upward or downwardly. Similarly, the armboards may be pivoted inwardly and outwardly in a horizontal plane with respect to the main body section. The head and foot sections are pivotal about horizontal axes adjacent to the upper and lower edges of the main body section while the armboards are pivotal about vertical axis located adjacent to the sides of the main body section.

Positioned on the operating table is the main cover 28 which is formed with an enlarged planar surface 50, rectangular in the lower portion 52 and central portion 54 to correspond with the rectangular nature of the foot section and main body section of the operating table. The head portion 56 of the main sheet extends outwardly from the main body portion but it is angled inwardly to correspond to the tapering of the head section of the operating table. Extending downwardly from the horizontal portion of the sheet are vertical sides or edges 16 which are pulled together at the corners of the head and foot ends and at the regions which are to be bent with the bending of the table. The sheets then turn inwardly at edges 18 terminating at the periphery for being supported on the main section of the operating table. A thread or strand 32 of elastomeric material is then positioned for free movement in the peripheral edge of the sheet. The periphery and its stitched or otherwise adhered elastic are adapted to be located beneath the operating table when in operation and use.

At the side edges of the sheet, at those regions 60 and 62 where the foot portion contacts the main body portion and the head portion contacts the main body portion, the sheet material is further gathered from the excess material of the corners to allow for expansion and contraction of the side and bottom portions of the sheets to accommodate the bending of the sheets along with the operating table during operation and use. The material from the gathered corners is extended into the bend regions and is adhered or stitched to the elastic in such orientation and position to accommodate bending. In this manner, the sheet may readily be put on the table or taken off and bent with the bending of the operating table, all without ripping under the stretching.

In an alternate embodiment of the invention, the elastic 64 is held to the periphery by being freelocated within a hem 66 extending around the entire periphery, not stitched or adhered thereto. The material from the gathered corners is extended into the sheet corners and bend regions.

Each arm board 36 is provided with its own separate paper or other non-woven, inextensible sheet 30 which is similar in construction to the cover on the operating table. The side sheets are of an elongated configuration to correspond to the size and shape of the armboards. Here again the sheet material is planar at its upper surface and extends downwardly in side walls where it is gathered at its corners and bent inwardly beneath the armboards terminating at a periphery 68. And again, the periphery is provided with a strand of elastomeric material 32. Such elastic may be adhered to the periphery as shown in FIG. 9 or positioned within a hem as described with respect to the sheet on the operating table. As a further embodiment, the elastic may be replaced by a drawstring 74 through a hem 76 at one end of the sideboard sheet.

As can be seen in FIGS. 1 and 8, the side arms of the operating table are of the type having a linear construction with a linear extent several times greater than the circumference of the side arms. Similarly, when a tubular shaped cover or sheet, as shown in the FIG. 8 embodiment, is placed over its associated side arm, it will assume a linear configuration. Further, like the side arm, it has a linear extent several times greater than its circumference. Each side arm sheet has a closed first end adjacent the free first end of the side arm with a second open end positionable adjacent to the table for sliding the sheet on and off the side arm.

From a size standpoint, the operating table has width of about 50 cm, a thickness of about 5 cm, and a length of about 176 cm with the head section being 24 cm, the body section being about 109 cm and the foot section being about 43 cm. Each arm board has a length of about 66 cm, a thickness of about 6 cm, and a width of about 15 cm.

The preferred material for the sheets is a drapable, absorbant material simulating the properties of woven cloth of which sheets are normally made. Paper has been found to be acceptable. Also acceptable is the synthetic, non-woven material as described in the U.S. patent to Brock, referenced hereinable, the subject matter of which is incorporated herein by reference.

While the present invention has been described as being carried out in a particular embodiment hereof, it is intended to be covered broadly within the spirit and scope of the appended claims.

What is claimed is:

1. A sheeting system for covering an operating table which includes a main body section with a head section and a foot section pivotally coupled about horizontal axes to the main body section, and with side arms pivotally coupled about vertical axes to the main body section, the sheeting system including:
    a single large sheet positionable over the main body section, head section and foot section formed of a non-woven fabric having an enlarged planar portion, downwardly turned edges and an inwardly turned periphery with elastomeric material coupled to at least portions of the periphery whereby the edges and periphery accommodate the bending of the sheet along its side edges with the bending of the operating table; and
    a pair of small sheets positionable over the side arms, the small sheets being formed of a non-woven material with an enlarged planar portion, downwardly turned edges and inwardly turned portions.

2. The system as set forth in claim 1 wherein the inwardly turned portion terminates in a periphery with a piece of elastomeric material attached to the periphery.

3. The system as set forth in claim 1 wherein the inwardly turned portion terminates in a periphery with a hem and a piece of elastomeric material within the hem.

4. The system as set forth in claim 1 wherein the small sheets are formed in a tubular configuration.

5. The system as set forth in claim 1 wherein the elastomeric material is attached to spaced portions of the periphery of the large sheet.

6. The system as set forth in claim 1 wherein the elastomeric material is a single member located in a hem around the entire periphery of the large sheet.

7. In combination with an operating table having a main body section with a head section and a foot section pivotally coupled about horizontal axes to the main body section, and with side arms pivotally coupled about vertical axes to the main body section, an improved system for covering both the side arms and the operating table, the covering for the side arms being a pair of small sheets of non-woven material, and the covering for the operating table being a single sheet formed of a non-woven material having an enlarged planar portion, downwardly turned sides and an inwardly turned periphery with a piece of elastomeric material coupled to the periphery at the corners and at least partially down the sides to accommodate bending.

8. The combination as set forth in claim 7 wherein the sheet is of a non-extensible material.

9. The combination as set forth in claim 7 wherein the sheet is a single layer of paper.

10. The combination as set forth in claim 7 wherein the sheet includes a synthetic material.

11. The combination as set forth in claim 7 wherein the inwardly turned portion terminates in a periphery with pieces of elastomeric material attached to the periphery at spaced apart regions.

12. The combination as set forth in claim 11 wherein the pieces of elastomeric material include a large piece extending from one side, around the head end and down the other side and a pair of small pieces on opposite sides.

13. The combination as set forth in claim 7 wherein the inwardly turned portion terminates in a periphery with a hem and a single piece of elastomeric material within the hem.

14. In combination with side arms of an operating table, apparatus for covering such side arms comprising a pair of sheets in a tubular configuration, each sheet having an opening at one end with peripheral means thereadjacent to constrict the opening and secure the sheet to its associated side arm, each sheet being fabricated of a non-woven, inextensible fabric.

15. The apparatus as set forth in claim 14 wherein the peripheral means is a cord in a hem at the opening.

16. In combination with an operating table having a pair of side arms, each side arm being of the type having a linear extent several times greater than its circumference and having a free first end and a second end coupled to the operating table, a pair of sheets for covering such side arms, each sheet being constructed in a tubular, linear configuration, with a linear extent several times greater than its circumference, each sheet being closed at its first end and having an opening at its second end to slide over an associated side arm and firmly secure the sheet to its associated side arm, each sheet being fabricated at a non-woven fabric.

* * * * *